(12) United States Patent
Keri et al.

(10) Patent No.: US 7,220,357 B2
(45) Date of Patent: May 22, 2007

(54) METHOD OF PURIFYING MACROLIDES

(75) Inventors: Vilmos Keri, Debrecen (HU); Zoltan Czövek, Debrecen (HU); Andrea Csorvasi, Debrecen (HU); Ferenc Rantal, Debrecen (HU)

(73) Assignee: Teva Gyógyszergyár Zártkörúen Múkó dó Résvénytársaság, Debrecen (HU)

( * ) Notice: Subject to any disclaimer, the term of this patent is extended or adjusted under 35 U.S.C. 154(b) by 33 days.

(21) Appl. No.: 10/899,757

(22) Filed: Jul. 26, 2004

(65) Prior Publication Data

US 2005/0027112 A1  Feb. 3, 2005

Related U.S. Application Data

(60) Provisional application No. 60/539,363, filed on Jan. 26, 2004, provisional application No. 60/490,070, filed on Jul. 24, 2003.

(51) Int. Cl.
*B01D 15/08* (2006.01)

(52) U.S. Cl. ............ 210/635; 210/656; 540/456; 540/458; 549/263

(58) Field of Classification Search ............ 210/635, 210/656, 659, 198.2; 540/456, 458; 549/263
See application file for complete search history.

(56) References Cited

U.S. PATENT DOCUMENTS

| | | | |
|---|---|---|---|
| 3,993,749 | A | 11/1976 | Sehgal et al. |
| 4,160,861 | A | 7/1979 | Cole et al. |
| 4,894,366 | A | 1/1990 | Okuhara et al. |
| 5,091,389 | A | 2/1992 | Ondeyka et al. |
| 5,116,756 | A | 5/1992 | Dumont et al. |
| 5,200,505 | A | 4/1993 | Takesako et al. |
| 5,496,727 | A | 3/1996 | Okuhara et al. |
| 5,506,233 | A | 4/1996 | Hauske et al. |
| 5,508,398 | A | 4/1996 | Gletos |
| 5,622,866 | A | 4/1997 | Motamedi et al. |
| 5,624,842 | A | 4/1997 | Okuhara et al. |
| 6,387,258 | B1 | 5/2002 | Keri et al. |
| 6,576,135 | B1 * | 6/2003 | Higaki et al. ............ 210/635 |
| 2002/0128470 | A1 | 9/2002 | Fuenfschilling et al. |
| 2003/0166924 | A1 | 9/2003 | Keri et al. |
| 2004/0050782 | A1 | 3/2004 | Fuenfschilling et al. |
| 2005/0209192 | A1 * | 9/2005 | Aylward et al. ............ 514/63 |
| 2006/0105994 | A1 * | 5/2006 | Aylward et al. ............ 514/63 |

FOREIGN PATENT DOCUMENTS

| | | |
|---|---|---|
| CH | 692 839 A5 | 11/2002 |
| DE | 2121517 | 11/1972 |
| EP | 0 184 162 | 6/1986 |
| EP | 0 652 219 A1 | 5/1995 |
| EP | 1 234 833 A2 | 8/2002 |
| WO | WO 92/18506 | 10/1992 |
| WO | WO 00/33878 | 6/2000 |

OTHER PUBLICATIONS

The Merck Index, Maryadele J. O'Neil et al. eds., "Pimecrolimus", p. 1331, 13th ed. 2001.
Martindale: The complete drug reference, Sean C. Sweetman ed., "Sirolimus", p. 568, Pharmaceutical Press 33rd ed. 2002.
Martindale: The complete drug reference, Sean C. Sweetman ed., "Everolimus", p. 539, Pharmaceutical Press 33rd ed. 2002.
Zhiguo Song et al. "Highly Chemoselective Trichloracetimidate-Mediated Alkylation of Ascomycin: A Convergent, Practical Synthesis of the Immunosupporessant L-733,725" J. Org. Chem. 1999, v. 64, p. 1859-1867.
Jun'ichi Kobayashi et al. "Amphidinolides T2, T3, and T4, New 19-Membered Macrolides from the Dinoflagellate *Amphidinium* sp. and the Biosynthesis of Amphidinolide T1" J. Org. Chem. 2001, v. 66, p. 134-142.
K. Yoshii et al. "Liquid Chromatographic Determination of Emamectin, Milbemectin, Ivermectin and Abamectin in Crops and Confirmation by Liquid Chromatography—Mass Spectrometry" Journal of Chromatography A, v. 896, 2000, p. 75-85.
C.E.M. Griffiths "Ascomycin: An Advance in the Management of Atopic Dermatitis" British J. of Dermatology, V. 144, p. 679-681, (2001).
Surjit S. Sengha, Fermentation, in Kirk Othmer Encyclopedia of Chemical Technology, vol. 10, p. 361-381 (Jacquiline I. Kroschwitz, editor. 4th ed. 1993).
Patent Abstract of Japan Publication No. 02016662; Publication date Jan. 19, 1990; Akashi Kazuya "Substituting Terminal Controller".

* cited by examiner

*Primary Examiner*—Ernest G. Therkorn
(74) *Attorney, Agent, or Firm*—Kenyon & Kenyon LLP

(57) ABSTRACT

Provided is a method of purifying a macrolide, especially tacrolimus, that includes loading macrolide onto a bed of sorption resin and elting with a suitable eluent such as a combination of water and tetrahydrofuran.

41 Claims, No Drawings

METHOD OF PURIFYING MACROLIDES

RELATED APPLICATIONS

This application claims the benefits of U.S. provisional application Ser. No. 60/490,070, filed Jul. 24, 2003 and U.S. provisional application Ser. No. 60/539,363, filed Jan. 26, 2004, the contents of all of which are incorporated herein by reference.

The present invention relates to a method of purifying macrolides, especially tacrolimus, ascomycin, sirolimus, everolimus, or pimecrolimus, by a separation method using sorption resins.

BACKGROUND OF THE INVENTION

Macrolides are multi-membered lactone rings having one or more deoxy sugars as substituents. Erythromycin, azithromycin, and clarithromycin are macrolides that have bacteriostatic and/or bactericidal activity.

Tacrolimus (FK 506) is also a macrolide antibiotic that is also an immunosuppressive agent. More potent than cyclosporin, tacrolimus reportedly has a selective inhibitory effect on T-lymphocytes.

Pimecrolimus is a macrolactam and a ascomycin derivative that reportedly inhibits production of pro-inflammatory cytokines by T cells and mast cells. The Merck Index 1331 (Maryadele J. O'Neil et al. eds., 13th ed. 2001). Pimecrolimus is reportedly used as an immunosuppressant. Id.

Sirolimus, another macrolide, is reported to be an immunosuppressant. Sirolimus has been administered with cyclosporin and corticosteroids after transplantation to avoid graft rejection. Martindale: The Complete Drug Reference 568 (Sean C. Sweetman ed., Pharmaceutical Press 33rd ed. 2002).

Everolimus, a derivative of sirolimus, is reported to be an immunosuppressant used in organ transplantation. Martindale at 539.

The macrolides are typically obtained by fermentation, although synthetic routes to some are known. Macrolides, as obtained, typically contain several impurities that can be detected by various means, for example high-pressure liquid chromatography (HPLC). Presence of impurities in a pharmaceutical compound is undesirable, and health authorities in many jurisdictions (e.g. the Food and Drug Administration in the United States) have established guidelines relating to acceptable levels of impurities in pharmaceuticals. The need for and commercial utility of methods of reducing the level of impurities in any pharmaceutical are self-evident.

SUMMARY OF THE INVENTION

In one aspect, the present invention relates to a method of separating impurities from (i.e. reducing the level of impurities in) a macrolide, especially tacrolimus, ascomycin, sirolimus (rapamycin), everolimus, and pimecrolimus. The method includes the steps of: preparing a loading charge of a macrolide; loading the loading charge onto a bed of wet sorption resin; eluting the bed with an eluent that contains THF or acetonitrile, water, and optionally an additional organic solvent; collecting a main fraction (heart cut) of eluent, and isolating the macrolide having reduced impurities from the main fraction.

In another aspect, the present invention relates to mactolides prepared by the method described above, especially tacrolimus, ascomycin, sirolimus (rapamycin), everolimus, and pimecrolimus.

DETAILED DESCRIPTION OF THE INVENTION

As used herein, the term ambient temperature refers to a temperature of about 0° to about 40° C., preferably of about 10° to about 35° C.

As used herein, the term reduced pressure refers to a pressure of less than about 760 mm Hg.

As used herein, the term anti-solvent refers to a substance, normally liquid at ambient temperature, in which macrolide is at best sparingly soluble.

As used herein, the term "impurity" relates to any compound having a different retention time than the desired macrolide. The different retention time may be measured, for example, by the HPLC method described herein below.

As used herein, the terms RRT0.95 and RRT1.25 refer to ascomycin and dihydrotacrolimus, respectively, which are impurities in tacrolimus, having relative retention times (to tacrolimus) of about 0.95 and 1.25 in HPLC analysis, such as the one described herein below.

As used herein in connection with mixtures or combinations of liquids, the term volume percent or percent-by-volume (vol-%) refers to volume fraction calculated as follows (illustrated for species A):

$$\text{vol-}\%_A = Wt_A \times \rho_A / (Wt_A \times \rho_A + Wt_B \times \rho_B)$$

where:

$Wt_A$ and $Wt_B$ are the weights in grams of species A and B, respectively, and $\rho_A$ and $\rho_B$ are the densities, in g./ml. of species A and B, respectively.

In one embodiment, the present invention provides a chromatographic method for separating macrolides from impurities therein (i.e. for reducing the level of impurities in) a macrolide). Separation (reduction) is effected by loading the macrolide onto a bed of sorption resin and eluting with an eluent that contains THF or acetonitrile, water, and optionally an additional organic solvent. Preferred macrolides for the practice of the present invention include tacrolimus, ascomycin, sirolimus, everolimus, and pimecrolimus. When tacrolimus is the macrolide, the impurities reduced include at least ascomycin and dihydrotacrolimus, quantification of which by HPLC is described hereinbelow. When ascomycin is the macrolide, the impurities reduced include at least tacrolimus. The macrolide used can be from any source.

In the practice of the present invention, reduction (separation) is effected by eluting a bed of sorption resin, loaded with a loading charge of macrolide, with an eluent to obtain an effluent. The sorption resins useful in the practice of the present invention are well-known in the art and are preferably cross-linked, non-ionic styrene-divinyl benzene materials, but can be chemically modified. Acrylic-type sorption resins are also known. The sorption resins have highly porous structures whose surfaces can absorb—then desorb—various chemical species. The absorption and desorption are influenced by the environment, for example the solvent used. In the presence of polar solvents (e.g. water) the sorption resins exhibit hydrophobic behavior. When non-polar solvents are used (e.g. hydrocarbons), the sorption resins can exhibit some polar behavior. Typically, sorption resins have a macroreticular structure and have surface areas of at least about 300 m²/g.

Sorption resins useful in the practice of the present invention include the Amberlite® XAD resins available from Rohm and Haas; XAD 4, XAD 7 HP, XAD 16 HP, XAD 761, and XAD 1180, to mention just a few. Also useful are the Diaion sorption resins available from Mitsubishi; HP 10, HP 20, HP 21, HP 30, HP 40, HP 50, SP 800, SP 825, SP 850, SP 875, SP 205, SP 206, SP 207, HP1MG and HP2MG, to mention just a few. Amberlite® XAD 1180 is an example of a preferred sorption resin for use in the practice of the present invention. Amberlite XAD 1180 is a macroreticular crosslinked aromatic polymer. It is a non ionic, hydrophobic, crosslinked polymer which derives its adsorptive properties from its patented macroreticular structure (containing both a continuous polymer phase and a continuous pore phase), high surface area, and the aromatic nature of its surface. Surface area is 500 m2/g or higher. Porosity is 0.60 ml/ml or higher. Product data sheet of PDS 0205 A—Jan. 1998-½ gives further information about this resin.

In a first step of the method of the present invention, the loading charge of the macrolide is loaded onto a bed of sorption resin. The loading charge can be provided as a solution of the macrolide in an organic solvent, combined with an anti-solvent.

Alternatively, the loading charge of the macrolide is adsorbed onto (deposited onto) a loading portion of sorption resin prior to loading onto the bed of sorption resin. A solution of the macrolide in an organic solvent, optionally containing water, is combined with a portion of sorption resin and an anti-solvent. The sorption resin can be the same as that used to prepare the bed, or it can be a different sorption resin. The loading portion of sorption resin can be about 33% to about 50% the volume of the bed. The loading portion is then juxtaposed to a bed of wet sorption to provide a bed loaded with the loading charge.

The organic solvent used to prepare the solution from which the loading charge is loaded or deposited is preferably selected from the group consisting of tetrahydrofuran (THF), acetone acetonitrile (ACN), methanol, ethanol, n-butanol, n-propanol, iso-propanol, esters (e.g. ethyl acetate), and dipolar aprotic solvents such as dimethylformamide (DMF). Most preferably, the organic solvent is THF, acetone or ACN. When the macrolide is tacrolimus, THF and ACN are preferred solvents. Preferably, the anti-solvent is water or a straight or branched alkane or cycloalkane such as hexane, heptane or cyclohexane. Addition of an anti-solvent reduces the solubility of the macrolide in the solution, and, it is thought, facilitates adsorption of the sample onto the loading portion of sorption resin. The anti-solvent is added slowly to avoid large concentration gradients that can result in partial bulk precipitation of the macrolide, which can lead to fouling and plugging. Preferably, the solvent:anti-solvent ratio is 40% or less.

The combining of macrolide solution, loading portion of sorption resin, and anti-solvent can be in any convenient vessel equipped with an agitator (e.g. a stirred-tank reactor).

In a particular embodiment, the loading portion of sorption resin is contained in a column and is contacted with a flow of macrolide solution thorough the column in a recirculating system. Anti-solvent is gradually introduced into the stream of solution flowing through and around the loading portion of sorption resin, whereby the macrolide sample is gradually adsorbed onto the loading portion of sorption resin.

By way of example, when the macrolide is tacrolimus, the solution can be about 100 g/L and the volume of anti-solvent can be at least about five times the volume of solution. The bulk volume of the loading portion of sorption resin can be approximately equal to the volume of solution. The skilled artisan will know to optimize the proportions by routine experimentation to obtain adsorption of the macrolide on the loading portion of the sorption resin.

After adsorption is substantially complete, which can be monitored by monitoring the concentration of macrolide remaining in the solution, the loading charge is separated from the remaining solution. Separation can be by filtration. When the recirculating column method for making the loading charge is used, the column is simply decoupled from the recirculating system.

In a subsequent step of this embodiment, the now macrolide-loaded loading portion is juxtaposed to a prepared bed of wet sorption resin. The bed is confined in a suitable vessel. Preferably, the bed is confined within a column, preferably of circular crossection. To prepare the bed, the desired amount of sorption resin is slurried with water or a mixture of water and a solvent (e.g. THF or ACN). A water-solvent combination is advantageous when the bed is to have a large diameter. The slurry is then transferred to the desired vessel, preferably a cylindical column such as is used for column chromatography. The water (or water-solvent combination) is drawn-off to leave a bed of wet sorption resin. The practice of preparing and packing chromatography columns is well know to the skilled artisan and routiner alike, and the known practices are readily adapted to the practice of the present invention.

The loading portion can be juxtaposed to the bed of wet sorption resin simply as a layer thereon. When the loading charge is prepared in a recirculating system, the vessel containing the loading charge can be coupled to the container holding the bed of wet sorption resin by any means that establishes fluid communication therewith.

Separation of macrolide (e.g. tacrolimus, ascomycin, sirolimus, everolimus, or pimecrolimus) and impurities, whereby the level of impurities in the macrolide is reduced, is effected by passing an eluent through the loading charge and subsequently through the bed of sorption resin juxtaposed thereto and in fluid communication therewith.

The eluent includes water and an organic solvent such as THF or ACN. A preferred eluent, especially when tacrolimus is the macrolide, is essentially a mixture of THF and water having about 20 vol-% to about 50 vol-%, most preferably about 31 vol-% to about 40 vol-%, THF. When an organic solvent such as methanol, acetonitrile, acetone or n-butanol is used with the THF—water eluent, the THF content is less than 38 vol-%, preferably between about 4 and about 38 vol-%. Another preferred eluent is a mixture of acetonitrile and water having about 30 vol-% to about 70 vol-%, most preferably about 40 vol-% to about 65 vol-%, acetonitrile. When the eluent is a mixture of acetonitrile and water, the eluent can also include about 0.0005 to about 0.003 parts inorganic acid to 1 part eluent. A preferred inorganic acid is phosphoric acid.

The eluent is eluted through the loading portion and bed of sorption resin juxtaposed thereto at a rate that depends on the gross crossectional area of the bed (measured perpendicular to the flow of eluent). Preferably, the flow rate (relative to the crossectional area) is less than about 25 cm/h, preferably less than about 15 cm/h. Lower elution rates increase the time, but improve the separation efficiency. A preferred elution rate for increased separation efficiency is about 90 mL/hour.

The eluent flowing out of the bed of sorption resin (i.e. the effluent) is collected in one or more fractions, as in is customary to the skilled artisan using separation methods, like chromatography, that depend on preferential retention of chemical species on a stationary phase (e.g. a static bed). An inorganic acid, such as phosphoric acid, may be added to the effluent.

Preferably, after eluting the bed with an amount of eluent, the bed is placed in fluid communication with a second bed so that effluent from the first bed elutes through the second bed. After elution of first and second beds, the second bed can be and preferrably is decoupled from the first bed (i.e. fluid communication is broken) and elution is continued through the second bed alone. The eluent is a mixture of THF and water having about 33 vol-% to 35 vol-% THF and the preferred eluent Optionally, additional columns may be connected to the system.

The concentration and composition of the fractions can be monitored by any convenient means. Detection and quantification of impurities in a macrolide, in particular ascomycin and dihydrotacrolimus in tacrolimus, can be carried-out by the hereinbelow described HPLC method.

Depending on, inter alia, column loading and the composition and flow rate of the eluent, a main fraction (heart cut) of effluent including more than about 60%, preferably between about 60 weight % and about 90 weight % of the macrolide originally present in the solution is collected. When tacrolimus is the macrolide and THF—water (31 to 40 vol-% THF) is the eluent, the main fraction is collected do that the final isolated product has about 0.1 area % or less (by HPLC described below) of impurity RRT0.95.

If desired, the macrolide separated from impurities and therefore having a reduced level of impurities can be isolated from effluent by any conventional means (e.g. extraction, lyophilization, evaporation, addition of anti-solvent). Water, alkanes and cycloalkanes can be mentioned as useful anti-solvents. Isolation methods can be combined. For example anti-solvent can be combined with concentrated eluent.

A preferred method of isolation includes concentration of the main fraction at 70° C. or less, preferably 60° C. or less, preferably at pressure of 760 mm Hg, to about 50% of its initial volume, whereby crystals of product are obtained. Acid, about 1 to about 10 mL per litre of eluent is preferably added before concentration to stabilize the macrolide.

Optionally, the concentrated main fraction is maintained at ambient temperature for a holding time. When a holding time is used, a preferred holding time is about 1–4 days. The crystals of macrolide having reduced impurities are recovered by any conventional means, for example filtration (gravity or vacuum).

Further reduction in impurities can be achieved by subjecting the recovered product to several additional treatments according to the method of the present invention.

The reduction in impurities in a macrolide accomplished by the method of the present invention can be monitored by the HPLC method described hereinbelow.

In another embodiment, the macrolide is tacrolimus, and at least the levels of impurities ascomycin and dihydrotacrolimus are reduced. The levels of other impurities are also reduced. The method includes the steps of: preparing a loading charge of tacrolimus comprising a solution of tacrolimus with or without a loading portion of a sorption resin, especially a macroreticular nonionic synthetic polymer resin such as Amberlite® XAD 1180 and Diaion HP 20; loading the loading charge to wet sorption resin, especially Amberlite® XAD 1180 and Diaion HP 20 that can be contained in a vessel, especially a column; eluting the loading portion and sorption resin with an eluent that is a mixture of tetrahydrofuran (THF) and water, about 20 vol-% to about 50 vol-%, especially about 31 vol-% to about 40 vol-% THF, or a mixture of acetonitrile (ACN) and water, about 30 vol-% to about 70 vol-% and most especially about 40 vol-% to about 65 vol-% acetonitrile; collecting at least a main fraction (heart cut) of eluent that contains more than about 60%, preferably between about 60% and about 90% of the initial tacrolimus, (depending on the initial purity) and, optionally, isolating tacrolimus having reduced impurities from the main fraction by, for example, concentrating the main fraction(s), for example at reduced pressure in the presence of an acid, and optionally recovering the product so obtained.

In another embodiment, the present invention provides for tacrolimus, prepared according to the methods described above.

In yet another embodiment, the macrolide is ascomycin, and at least the levels of impurity tacrolimus is reduced. The levels of other impurities are also reduced. The method includes the steps of: preparing a loading charge of ascomycin comprising a solution of ascomycin with or without a loading portion of a sorption resin, especially a macroreticular nonionic synthetic polymer resin such as Amberlite® XAD 1180 and Diaion HP 20; loading the loading charge to wet sorption resin, especially Amberlite® XAD 1180 and Diaion HP 20 that can be contained in a vessel, especially a column; eluting the loading portion and sorption resin with an eluent that is a mixture of tetrahydrofuran (THF) and water, about 20 vol-% to about 50 vol-%, especially about 31 vol-% to about 40 vol-% THF, or a mixture of acetonitrile (ACN) and water, about 30 vol-% to about 70 vol-% and most especially about 40 vol-% to about 65 vol-% acetonitrile; collecting at least a main fraction (heart cut) of eluent that contains more than about 60%, preferably between about 60% and about 90% of the initial ascomycin, (depending on the initial purity) and, optionally, isolating ascomycin having reduced impurities from the main fraction by, for example, concentrating the main fraction(s), for example at reduced pressure in the presence of an acid, and optionally recovering the product so obtained.

In another embodiment, the present invention provides for ascomycin, prepared according to the methods described above.

In yet another embodiment, the macrolide is sirolimus. The method for separating impurities from sirolimus includes the steps of: preparing a loading charge of sirolimus comprising a solution of sirolimus with or without a loading portion of a sorption resin, especially a macroreticular resin such as Amberlite® XAD 1180 and Diaion HP 20; loading the loading charge to wet sorption resin, especially Amberlite® XAD 1180 and Diaion HP 20 that can be contained in a vessel, especially a column; eluting the loading portion and sorption resin with an eluent that is a mixture of tetrahydrofuran (THF) and water, about 20 vol-% to about 50 vol-%, especially about 31 vol-% to about 40 vol-% THF, or a mixture of acetonitrile (ACN) and water, about 30 vol-% to about 70 vol-% and most especially about 40 vol-% to about 65 vol-% acetonitrile; collecting at least a main fraction (heart cut) of eluent that contains more than about 60%, preferably between about 60% and about 90% of the initial sirolimus, (depending on the initial purity) and, optionally, isolating sirolimus having reduced impurities from the main fraction by, for example, concentrating the main fraction(s), for example at reduced pressure in the presence of an acid, and optionally recovering the product so obtained.

In another embodiment, the present invention provides for sirolimus, prepared according to the methods described above.

In yet another embodiment, the macrolide is everolimus. The method for separating impurities from everolimus includes the steps of: preparing a loading charge of everolimus comprising a solution of everolimus with or without a loading portion of a sorption resin, especially a macroreticular resin such as Amberlite® XAD 1180 and Diaion HP 20; loading the loading charge to wet sorption resin, especially Amberlite® XAD 1180 and Diaion HP 20 that can be contained in a vessel, especially a column; eluting the loading portion and sorption resin with an eluent that is a mixture of tetrahydrofuran (THF) and water, about 20 vol-% to about 50 vol-%, especially about 31 vol-% to about 40 vol-% THF, or a mixture of acetonitrile (ACN) and water, about 30 vol-% to about 70 vol-% and most especially about 40 vol-% to about 65 vol-% acetonitrile; collecting at least a main fraction (heart cut) of eluent that contains more than about 60%, preferably between about 60% and about 90% of the initial everolimus, (depending on the initial purity) and, optionally, isolating everolimus having reduced impurities from the main fraction by, for example, concentrating the main fraction(s), for example at reduced pressure in the presence of an acid, and optionally recovering the product so obtained.

In another embodiment, the present invention provides for everolimus, prepared according to the methods described above.

In yet another embodiment, the macrolide is pimecrolimus. The method for separating impurities from pimecrolimus includes the steps of: preparing a loading charge of pimecrolimus comprising a solution of pimecrolimus with or without a loading portion of a sorption resin, especially a macroreticular resin such as Amberlite® XAD 1180 and Diaion HP 20; loading the loading charge to wet sorption resin, especially Amberlite® XAD 1180 and Diaion HP 20 that can be contained in a vessel, especially a column; eluting the loading portion and sorption resin with an eluent that is a mixture of tetrahydrofuran (THF) and water, about 20 vol-% to about 50 vol-%, especially about 31 vol-% to about 40 vol-% THF, or a mixture of acetonitrile (ACN) and water, about 30 vol-% to about 70 vol-% and most especially about 40 vol-% to about 65 vol-% acetonitrile; collecting at least a main fraction (heart cut) of eluent that contains more than about 60%, preferably between about 60% and about 90% of the initial pimecrolimus, (depending on the initial purity) and, optionally, isolating pimecrolimus having reduced impurities from the main fraction by, for example, concentrating the main fraction(s), for example at reduced pressure in the presence of an acid, and optionally recovering the product so obtained.

In another embodiment, the present invention provides for pimecrolimus, prepared according to the methods described above.

Chromatographic conditions:

| Column: | ZORBAX SB-C18 75 × 4.6 mm; 3.5 μm |
|---|---|
| Pre-column: | SymmetryShield RP18 3.9 × 20 mm; 5 μm |
| Eluent: | A: Measure 200 ml of acetonitrile into a 2000 mL volumetric flask, then dilute to volume with distilled water to 2000 mL total volume. Then, add 100 μl of 50% acetic acid. |
| | B: Add 100 μl 50% acetic acid to 2000 ml of acetonitrile. |

Table of gradients

| Time (min) | Eluent "A" (w/w %) | Eluent "B" (w/w %) | Flow rate (ml/min) |
|---|---|---|---|
| 0 | 60 | 40 | 2.3 |
| 15 | 55 | 45 | 2.3 |
| 25 | 30 | 70 | 1.8 |
| 25, 1 | 60 | 40 | 1.8 |
| 27 | 60 | 40 | 1.8 |

| Flow rate: | 2.3 ml/min |
|---|---|
| Detection wavelenght: | 210 nm |
| Injected volume: | 20 μl |
| Sample's solvent: | acetonitrile |
| Temp. of column unit: | 60° C. |
| Analysis time: | 27 min |
| Retention time of tacrolimus: | appr. 14 min. |

Retention times of impurities ascomycin (RRT0.95) and dihydrotacrolimus (RRT1.25) are relative to tacrolimus and expressed as an area percent relative to the area of all peaks in the chromatogram.

Retention times of the impurity tacrolimus (RRT1.00) is relative to ascomycin and expressed as an area percent relative to the area of all peaks in the chromatogram.

The method of the present invention can be exemplified by the following non-limited examples.

EXAMPLE 1

Area percents refer to area percent of HPLC chromatograms obtained by the hereinabove described method.

The procedure below was carried-out at 28° C. to 32° C.

A bed of sorption resin (Amberlite® XAD 1180) in a column (45 cm diameter) using water:THF to charge the column (ca. 100 L wet sorption resin) was prepared.

Water (86 L) was slowly added, with agitation, to a solution of tacrolimus (1227 g) in acetonitrile (10 L) in which sorption resin (Amberlite® XAD 1180; 9 L) was suspended with stirring. The tacrolimus used contained about 2.6 area-% RRT0.95 and about 2.9 area-% RRT1.25. When the addition of water was complete, the loading charge of sorption resin was collected by filtration.

The collected loading charge was loaded (juxtaposed) as a layer on top of the bed of wet sorption resin.

The column was first eluted with ca. 1800 L of a first eluent made-up of THF/water (33 vol-% THF). The column was then eluted with second eluent made-up of THF/water (40 vol-% THF). The elution rate was about 11 to 13 L/hr (6.9 to 8.2 cm/hr). A main fraction, ca 460 L containing about 820 g tacrolimus (67% yield) was collected. A pre-fraction, ca. 80 L, containing ca. 190 g tacrolimus, was also collected.

The main fraction (460 L) was combined with phosphoric acid, 85% (460 mL), and concentrated at reduced pressure to a volume of about 230 L. The concentrate was held at ambient temperature for one day. (N.b., longer holding times were tried in subsequent experiments. The crystals obtained were more easily filtered than those obtained here). The crystals were washed with hexane and dried at 40° C.

The product isolated from the main fraction had about 0.1 area-% RRT0.95 and about 1.7 area-% RRT1.25.

The product isolated from the pre-fraction had about 3 area-% RRT0.95 and about 0.3 area-% RRT1.25.

EXAMPLE 2

The general procedure of example 1 was repeated to investigate the effect of eluent composition and flow rate.

Through these experiments, we could establish that elution flow rate reduction increases the separation efficiency of the chromatography. Increasing the elution flow rate reduced the efficiency of the chromatography. Flow rate of 25 cm/cm².hour (instead of 6.9 –8.2 cm/cm².hour) resulted in significant reductionb in efficiency, but main fraction of having the quality of that described in Example 1 could be collected.

It was further established that first eluent of 34% by volume THF (instead of 33% by volume) increased the yield of chromatography. The yield was 69%. Impurity RRT:0.95 level of main fraction was 0.10 area %.

When an eluent having 31 vol-% THF was used, elution time of tacrolimus was increased. The mentioned eluent concentrations (31%, 33%, 34%, 40% by volume tetrahydrofuran) were found usable for elution of tacrolimus, without increasing of solvent concentration.

These further experiments also established that eluent mixtures of water:tetrahydrofurane:solvents were also effective. Tested solvents used for water:tetrahydrofurane:solvent eluents were methanol, acetonitrile, acetone, n-propanol and n-butanol. Suitable quality was obtained in all cases.

EXAMPLE 3

Area percents refer to area percent of HPLC chromatograms obtained by the hereinabove described method.

The procedure below was carried out at 20° C. to 25° C.

A bed of sorption resin (Diaion SP 207) in a column (3.2 cm diameter) using water to charge the column (ca. 550 mL wet sorption resin) was prepared.

Tacrolimus (7.2 g) was dissolved in a mixture of acetonitrile (30 mL) and water (20 mL). The tacrolimus contained about 2.6 area-% RRT0.95 (ascomycin) and about 2.9 area-% RRT1.25 (dihydrotacrolimus).

The tacrolimus solution was loaded as layer on top of the bed of wet sorption resin.

The column was eluted with ca. 8 L of eluent made up of acetonitrile/water/phosphoric acid (600:400:1). The elution rate was 90 mL/hour.

Fractions 32–45 were combined. The combined fractions contained 1.9 g of tacrolimus. The impurity content of the combined fractions was about 2.9 area-% RRT0.95 (ascomycin) and about 1.2 area-% RRT1.25 (dihydrotacrolimus).

The described purification process is suitable for reduction of dihydrotacrolimus. Preferably, the eluent has an acetonitrile content of about 30% to 70%, preferably about 40% to 65%.

Inorganic acid content is used to prevent the decomposition of tacrolimus during the chromatography. Preferably, the inorganic acid is phosphoric acid. Preferably, the phosphoric acid content is between about 0.0005 to 0.003 parts acid to 1 part eluent.

The described purification process increases the efficiency of the processes described by examples 1 and 2.

EXAMPLE 4

Two columns were prepared for chromatography according to example 1. Before the chromatography, 3000 g active substance containing tacrolimus was adsorbed on sorption resin XAD 1180 according to the following procedure. The tacrolimus was dissolved in 15 L acetone. Sorption resin (33 L) was added to the solution, and 90 L water was added slowly to the solution/resin mixture with continuous stirring. The loading charge of sorption resin was headed juxtaposed) as a layer on the top of sorption resin contained in the first column.

The first column was eluted with tetrahydrofuran:water mixture (34 vol-% THF). The elution rate was 15 L/hour. Fractions of 20 L each were collected. Volume of each fraction was 20 L. After elution of the 35th fraction, the second column was connected (fluidly coupled) in series to the first column, and the elution was continued on columns in series.

After the 95th fraction eluted, the first column was disconnected, and the elution was continued only on the second column. The purified, suitable fractions were combined.

The major part of THF was removed from the combined fractions by evaporation under reduced pressure. The concentrate was extracted with ethylacetate and the phases separated. The separated ethylacetate phase was concentrated under reduced pressure (appr. 1 part tacrolimus and 1 part ethylacetate). Cyclohexane and water were added slowly to the concentrated ethyl acetate extract. The precipitated tacrolimus was recovered from the mixture at 0–30 C. The crystals were filtered and dried.

The starting substance contained appr. 0.5 area % ascomycin (RRT 0.95) and appr. 1.3% dihydrotacrolimus (RRT 1.25). The produced crystals contained less than 0.1 area % ascomycin and appr. 0.4 area % dihydrotacrolimus.

EXAMPLE 5

Tacrolimus was dissolved in a water:tetrahydrofurane (67 volume:33 volume) mixture. The achieved solvent concentration was appr. 30 g/litres. The solution was passed onto sorption resin XAD 1180. The sorption resin adsorbed the tacrolimus.

After adsorption, the elution of tacrolimus continued as in example 1.

EXAMPLE 6

Tacrolimus is dissolved in a water:tetrahydrofurane (67 volume:33 volume) mixture. The achieved solvent concentration is appr. 30 g/litres. The solution is passed onto sorption resin HP20. The sorption resin adsorbs the tacrolimus.

After adsorption, the elution of tacrolimus continues as in example 1.

EXAMPLE 7

The procedure below is carried-out at 28° C. to 32° C.

A bed of sorption resin (Amberlite® XAD 1180) in a column (45 cm diameter) using water:THF to charge the column (ca. 100 L wet sorption resin) is prepared.

Water (86 L) is slowly added, with agitation, to a solution of ascomycin (1227 g) in acetonitrile (10 L) in which sorption resin (Amberlite® XAD 1180; 9 L) is suspended with stirring. The ascomycin used contains RRT1.00 (tacrolimus). When the addition of water is complete, the loading charge of sorption resin is collected by filtration.

The collected loading charge is loaded juxtaposed) as a layer on top of the bed of wet sorption resin.

The column is first eluted with ca. 1800 L of a first eluent made-up of THF/water (33 vol-% THF). The column is then eluted with second eluent made-up of THF/water (40 vol-% THF). The elution rate is about 11 to 13 L/hr (6.9 to 8.2 cm/hr). A main fraction, ca 460 L containing ascomycin is collected. A pre-fraction, ca. 80 L, containing ascomycin, is also collected.

The main fraction (460 L) is combined with phosphoric acid, 85% (460 mL), and concentrated at reduced pressure to a volume of about 230 L. The concentrate is held at ambient temperature for one day. The crystals are washed with hexane and dried at 40° C.

EXAMPLE 8

Two columns are prepared for chromatography according to example 1.

Before the chromatography, 3000 g active substance containing ascomycin is adsorbed on sorption resin XAD 1180 according to the following procedure. The ascomycin is dissolved in 15L acetone. Sorption resin (33 L) is added to the solution, and 90 L water is added slowly to the solution/resin mixture with continuous stirring. The loading charge of sorption resin is headed (juxtaposed) as a layer on the top of sorption resin contained in the first column.

The first column is eluted with tetrahydrofuran:water mixture (34 vol-% THF). The elution rate is 15 L/hour. Fractions of 20 L each are collected. Volume of each fraction was 20 L. After elution of the 35th fraction, the second column is connected (fluidly coupled) in series to the first column, and the elution is continued on columns in series.

After the 95th fraction eluted, the first column is disconnected, and the elution is continued only on the second column. The purified, suitable fractions are combined.

The major part of THF is removed from the combined fractions by evaporation under reduced pressure. The concentrate is extracted with ethylacetate and the phases separated. The separated ethylacetate phase is concentrated under reduced pressure (appr. 1 part ascomycin and 1 part ethylacetate). Cyclohexane and water are added slowly to the concentrated ethyl acetate extract. The precipitated ascomycin is recovered from the mixture at 0–30° C. The crystals are filtered and dried.

EXAMPLE 9

The procedure below is carried-out at 28° C. to 32° C.

A bed of sorption resin (Amberlite® XAD 1180) in a column (45 cm diameter) using water:THF to charge the column (ca. 100 L wet sorption resin) is prepared.

Water (86 L) is slowly added, with agitation, to a solution of sirolimus (1227 g) in acetonitrile (10 L) in which sorption resin (Amberlite® XAD 1180; 9 L) is suspended with stirring. The sirolimus used contains impurities. When the addition of water is complete, the loading charge of sorption resin is collected by filtration.

The collected loading charge is loaded (juxtaposed) as a layer on top of the bed of wet sorption resin.

The column is first eluted with ca. 1800 L of a first eluent made-up of THF/water (33 vol-% THF). The column is then eluted with second eluent made-up of THF/water (40 vol-% THF). The elution rate is about 11 to 13 L/hr (6.9 to 8.2 cm/hr). A main fraction, ca 460 L containing sirolimus is collected. A pre-fraction, ca. 80 L, containing sirolimus, is also collected.

The main fraction (460 L) is combined with phosphoric acid, 85% (460 mL), and concentrated at reduced pressure to a volume of about 230 L. The concentrate is held at ambient temperature for one day. The crystals are washed with hexane and dried at 40° C.

EXAMPLE 10

Two columns are prepared for chromatography according to example 1.

Before the chromatography, 3000g active substance containing sirolimus is adsorbed on sorption resin XAD 1180 according to the following procedure. The sirolimus is dissolved in 15 L acetone. Sorption resin (33 L) is added to the solution, and 90 L water is added slowly to the solution/resin mixture with continuous stirring. The loading charge of sorption resin is headed (juxtaposed) as a layer on the top of sorption resin contained in the first column.

The first column is eluted with tetrahydrofuran:water mixture (34 vol-% THF). The elution rate is 15 L/hour. Fractions of 20 L each are collected. Volume of each fraction was 20 L. After elution of the 35th fraction, the second column is connected (fluidly coupled) in series to the first column, and the elution is continued on columns in series.

After the 95th fraction eluted, the first column is disconnected, and the elution is continued only on the second column. The purified, suitable fractions are combined.

The major part of THF is removed from the combined fractions by evaporation under reduced pressure. The concentrate is extracted with ethylacetate and the phases separated. The separated ethylacetate phase is concentrated under reduced pressure (appr. 1 part sirolimus and 1 part ethylacetate). Cyclohexane and water are added slowly to the concentrated ethyl acetate extract. The precipitated sirolimus is recovered from the mixture at 0–30° C. The crystals are filtered and dried.

EXAMPLE 11

The procedure below is carried-out at 28° C. to 32° C.

A bed of sorption resin (Amberlite® XAD 1180) in a column (45 cm diameter) using water:THF to charge the column (ca. 100 L wet sorption resin) is prepared.

Water (86 L) is slowly added, with agitation, to a solution of everolimus (1227 g) in acetonitrile (10 L) in which sorption resin (Amberlite® XAD 1180; 9 L) is suspended with stirring. The everolimus used contains impurities. When the addition of water is complete, the loading charge of sorption resin is collected by filtration.

The collected loading charge is loaded (juxtaposed) as a layer on top of the bed of wet sorption resin.

The column is first eluted with ca. 1800 L of a first eluent made-up of THF/water (33 vol-% THF). The column is then eluted with second eluent made-up of THF/water (40 vol-% THF). The elution rate is about 11 to 13 L/hr (6.9 to 8.2 cm/hr). A main fraction, ca 460 L containing everolimus is collected. A pre-fraction, ca. 80 L, containing everolimus, is also collected.

The main fraction (460 L) is combined with phosphoric acid, 85% (460 mL), and concentrated at reduced pressure to a volume of about 230 L. The concentrate is held at ambient temperature for one day. The crystals are washed with hexane and dried at 40° C.

EXAMPLE 12

Two columns are prepared for chromatography according to example 1.

Before the chromatography, 3000 g active substance containing everolimus is adsorbed on sorption resin XAD 1180 according to the following procedure. The everolimus is dissolved in 15 L acetone. Sorption resin (33 L) is added to the solution, and 90 L water is added slowly to the solution/resin mixture with continuous stirring. The loading charge of sorption resin is headed (juxtaposed) as a layer on the top of sorption resin contained in the first column.

The first column is eluted with tetrahydrofuran:water mixture (34 vol-% THF). The elution rate is 15 L/hour. Fractions of 20 L each are collected. Volume of each fraction was 20 L. After elution of the 35th fraction, the second column is connected (fluidly coupled) in series to the first column, and the elution is continued on columns in series.

After the 95th fraction eluted, the first column is disconnected, and the elution is continued only on the second column. The purified, suitable fractions are combined.

The major part of THF is removed from the combined fractions by evaporation under reduced pressure. The concentrate is extracted with ethylacetate and the phases separated. The separated ethylacetate phase is concentrated under reduced pressure (appr. 1 part everolimus and 1 part ethylacetate). Cyclohexane and water are added slowly to the concentrated ethyl acetate extract. The precipitated everolimus is recovered from the mixture at 0–30° C. The crystals are filtered and dried.

EXAMPLE 13

The procedure below is carried-out at 28° C. to 32° C.

A bed of sorption resin (Amberlite® XAD 1180) in a column (45 cm diameter) using water:THF to charge the column (ca. 100 L wet sorption resin) is prepared.

Water (86 L) is slowly added, with agitation, to a solution of pimecrolimus (1227 g) in acetonitrile (10 L) in which sorption resin (Amberlite® XAD 1180; 9 L) is suspended with stirring. The pimecrolimus used contains impurities. When the addition of water is complete, the loading charge of sorption resin is collected by filtration.

The collected loading charge is loaded (juxtaposed) as a layer on top of the bed of wet sorption resin.

The column is first eluted with ca. 1800 L of a first eluent made-up of THF/water (33 vol-% THF). The column is then eluted with second eluent made-up of THF/water (40 vol-% THF). The elution rate is about 11 to 13 L/hr (6.9 to 8.2 cm/hr). A main fraction, ca 460 L containing pimecrolimus is collected. A pre-fraction, ca. 80 L, containing pimecrolimus, is also collected.

The main fraction (460 L) is combined with phosphoric acid, 85% (460 mL), and concentrated at reduced pressure to a volume of about 230 L. The concentrate is held at ambient temperature for one day. The crystals are washed with hexane and dried at 40° C.

EXAMPLE 14

Two columns are prepared for chromatography according to example 1.

Before the chromatography, 3000g active substance containing pimecrolimus is adsorbed on sorption resin XAD 1180 according to the following procedure. The pimecrolimus is dissolved in 15 L acetone. Sorption resin (33 L) is added to the solution, and 90 L water is added slowly to the solution/resin mixture with continuous stirring. The loading charge of sorption resin is headed (juxtaposed) as a layer on the top of sorption resin contained in the first column.

The first column is eluted with tetrahydrofuran:water mixture (34 vol-% THF). The elution rate is 15 L/hour. Fractions of 20 L each are collected. Volume of each fraction was 20 L. After elution of the 35th fraction, the second column is connected (fluidly coupled) in series to the first column, and the elution is continued on columns in series.

After the 95th fraction eluted, the first column is disconnected, and the elution is continued only on the second column. The purified, suitable fractions are combined.

The major part of THF is removed from the combined fractions by evaporation under reduced pressure. The concentrate is extracted with ethylacetate and the phases separated. The separated ethylacetate phase is concentrated under reduced pressure (appr. 1 part pimecrolimus and 1 part ethylacetate). Cyclohexane and water are added slowly to the concentrated ethyl acetate extract. The precipitated pimecrolimus is recovered from the mixture at 0–30° C. The crystals are filtered and dried.

What is claimed is:

1. A method of separating a tacrolimus from impurities therein comprising the steps of:
    a) providing a loading charge of a tacrolimus having an initial level of impurities,
    b) loading the loading charge to a bed of sorption resin,
    c) eluting the bed of loaded sorption resin with an eluent comprising water and an organic solvent selected from tetrahydrofuran and acetonitrile, to obtain an effluent, and
    d) collecting at least one fraction of effluent comprising the tacrolimus.

2. The method of claim 1, wherein the loading charge of a tacrolimus further contains a loading portion of a sorption resin.

3. The method of claim 2 wherein the loading charge is loaded onto the loading portion of sorption resin in a recirculating system.

4. The method of claim 3, wherein the loading charge is deposited on the loading portion from its solution in an organic solvent in a step that includes combining the solution with an anti-solvent.

5. The process of claim 4, wherein the organic solvent is selected from the group consisting of tetrahydrofuran, acetone, acetonitrile, methanol, ethanol, n-butanol, n-propanol, iso-propanol, esters and dipolar aprotic solvents.

6. The process of claim 5, wherein the organic solvent is selected from the group consisting of tetrahydrofuran, acetone and acetonitrile.

7. The process of claim 4, wherein the anti-solvent is selected from the group consisting of water, straight or branched alkanes, or cycloalkanes.

8. The process of claim 7, wherein the anti-solvent is water.

9. The process of claim 4, wherein the ratio of combined solution to combined anti-solvent is 40% or less.

10. The method of claim 1 further comprising the step of isolating the tacrolimus from the at least one fraction, wherein the tacrolimus has a final level of impurities that is lower than the initial level of impurities.

11. The method of claim 10 wherein the isolating comprises the step of concentrating the at least one fraction at reduced pressure and a temperature of about 70° C. or below.

12. The method of claim 11 wherein the temperature is about 60° C. or below.

13. The method of claim 11 wherein the pressure is about 760 mm Hg.

14. The method of claim 11 further comprising the step of, prior to concentrating, combining the at least one fraction with an inorganic acid.

15. The method of claim 14 wherein the inorganic acid is phosphoric acid.

16. The method of claim 14 wherein the amount of the acid is 1 to about 10 mL per liter of eluent.

17. The method of claim 10 wherein the isolating comprises the step of combining an antisolvent with the at least one fraction of eluent.

18. The method of claim 17 wherein, prior to the combining, the at least one fraction of effluent is concentrated at reduced pressure.

19. The method of claim 1 wherein the sorption resin is a macroreticular resin.

20. The method of claim 19 wherein the sorption resin is a macroreticular nonionic synthetic polymer.

21. The method of claim 1 wherein the bed of sorption resin is confined in a column.

22. The method of claim 1 wherein the volume of effluent collected in at least one fraction comprises about 60% to about 100%, by weight, of the tacrolimus initially present in the loading charge.

23. The method of claim 1 wherein the eluent flow rate is less than about 25 cm/h.

24. The method of claim 23 wherein the eluent flow rate is less than about 15 cm/h.

25. The method of claim 1 wherein the eluent comprises a mixture of tetrahydrofuran and water having about 20 vol-% to about 50 vol-% tetrahydrofuran.

26. The method of claim 25 wherein the eluent has about 31 vol-% to about 40 vol-% tetrahydrofuran.

27. The method of claim 26 wherein the eluent has about 33 vol-% to about 35 vol-% tetrahydrofuran.

28. The method of claim 1 wherein the eluent comprises a mixture of acetonitrile and water having about 30 vol-% to about 70 vol-% acetonitrile.

29. The method of claim 28 wherein the eluent has about 40 vol-% to about 65 vol-% acetonitrile.

30. The method of claim 28 wherein the eluent includes up to about 0.003 parts of an inorganic acid per 1 part eluent, by volume.

31. The method of claim 30, wherein the inorganic acid is phosphoric acid.

32. The method of claim 1 wherein at least one additional bed of sorption resin is connected to the bed of sorption resin of step b.

33. The method of claim 32 wherein after additional series of eluent fractions the bed of resin of step b is disconnected.

34. A method of separating tacrolimus from impurities ascomycin and dihydrotacrolimus therein comprising the steps of:
   a) providing a loading charge of a tacrolimus having an initial level of impurities ascomycin and dihydrotacrolimus on a loading portion of a sorption resin that is a macroreticular resin,
   b) juxtaposing the loading portion bearing the loading charge of tacrolimus to a bed of sorption resin,
   c) eluting the loading portion and bed juxtaposed thereto with an eluent comprising water and an organic solvent selected from tetrahydrofuran and acetonitrile to obtain an effluent,
   d) collecting at least one fraction of effluent, and
   e) isolating tacrolimus having a final level of impurities ascomycin and dihydrotacrolimus from the at least one fraction, wherein the final level of impurities ascomycin and dihydrotacrolimus is lower than the initial level of these impurities.

35. The method of claim 34 wherein the eluent comprises a mixture of tetrahydrofuran and water having about 20 vol-% to about 50 vol-% tetrahydrofuran.

36. The method of claim 35 wherein the eluent comprises a mixture of tetrahydrofuran and water having about 31 vol-% to about 40 vol-% tetrahydrofuran.

37. The method of claim 36 wherein the mixture has about 33 vol-% to about 35 vol-% tetrahydrofuran.

38. The method of claim 34 wherein the eluent comprises a mixture of acetonitrile and water having about 30 vol-% to about 70 vol-% acetonitrile.

39. The method of claim 38 wherein the eluent has about 40 vol-% to about 65 vol-% acetonitrile.

40. The method of claim 34 wherein the eluent further comprises up to about 0.003 parts of an inorganic acid per part of eluent, by volume.

41. The method of claim 40, wherein the inorganic acid is phosphoric acid.

* * * * *

UNITED STATES PATENT AND TRADEMARK OFFICE
CERTIFICATE OF CORRECTION

| | | |
|---|---|---|
| PATENT NO. | : 7,220,357 B2 | Page 1 of 1 |
| APPLICATION NO. | : 10/899757 | |
| DATED | : May 22, 2007 | |
| INVENTOR(S) | : Vilmos Kéri | |

It is certified that error appears in the above-identified patent and that said Letters Patent is hereby corrected as shown below:

<u>Column 14</u>

Line 40, change "claim 3" to --claim 2--

<u>Column 15</u>

Line 24, change "about 100%" to --about 90%--

Signed and Sealed this

Fifteenth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,220,357 B2 Page 1 of 1
APPLICATION NO. : 10/899757
DATED : May 22, 2007
INVENTOR(S) : Vilmos Kéri It is certified that error appears in the above-identified patent and that said Letters Patent is hereby corrected as shown below:

Column 14

Line 40, change "claim 3" to --claim 2--

Column 15

Line 24, change "about 100%" to --about 90%--

Signed and Sealed this

Twenty-ninth Day of April, 2008

JON W. DUDAS
*Director of the United States Patent and Trademark Office*